United States Patent [19]

Brown et al.

[11] Patent Number: 5,700,798
[45] Date of Patent: Dec. 23, 1997

[54] METHODS FOR USING BENZOXAZINES FOR TREATING ASTHMA

[75] Inventors: Frederick Jeffrey Brown; Keith Russell, both of Newark; Paul James Warwick, Jr., Wilmington, all of Del.

[73] Assignee: Zeneca Limited, London, England

[21] Appl. No.: 541,782

[22] Filed: Oct. 10, 1995

Related U.S. Application Data

[63] Continuation of Ser. No. 239,637, May 9, 1994, Pat. No. 5,486,515.

[30] Foreign Application Priority Data

May 12, 1993 [GB] United Kingdom .................. 9309716

[51] Int. Cl.⁶ .................................................. A61K 31/535
[52] U.S. Cl. ............................ 514/229.8; 514/230.5; 544/101; 544/105
[58] Field of Search .......................... 544/101, 105; 514/229.8, 230.5

[56] References Cited

U.S. PATENT DOCUMENTS

| | | | |
|---|---|---|---|
| 3,192,208 | 6/1965 | Easton et al. | 544/101 |
| 3,225,042 | 12/1965 | Dillard et al. | 544/101 |
| 3,763,153 | 10/1973 | Krapcho et al. | 544/101 |
| 3,821,377 | 6/1974 | Krapcho et al. | 544/101 |
| 4,892,872 | 1/1990 | Tahara et al. | 514/229.8 |
| 5,270,308 | 12/1993 | Shiraishi et al. | 514/229.8 |
| 5,278,158 | 1/1994 | Tsuzuki et al. | 514/229.8 |
| 5,486,515 | 1/1996 | Brown et al. | 514/229.8 |

FOREIGN PATENT DOCUMENTS

| | | |
|---|---|---|
| 0432893A2 | 6/1991 | European Pat. Off. . |
| 0500319A1 | 8/1992 | European Pat. Off. . |
| 0509845A1 | 10/1992 | European Pat. Off. . |
| WO 94/04521 | 3/1994 | WIPO . |

OTHER PUBLICATIONS

K. Russell et al., "A Highly Potent Series of Fluoroalkyl Benzoxazine Pyridine–N–Oxide Potassium Channel Opener," Bioorganic & Medicinal Chemistry Letters, 3(12), 2727–2728, 1993.

Ashely E. Fenwick "The Synthesis of 2,2–Bis(Trifluoromethyl)Benzopyran Derivatives: A New Route to an Important Class of Potassium Channel", *Tetrahedron Letters*, (1993), 34, No. 11, 1815–1818.

Hiroshi Koga et al. "Synthesis and Antihypertensive Activity of KC–399, A Benzopyran K+ Channel Opener with long Duration of Action and Less Tachycardia", *Bioorganic & Medicinal Chemistry Letters*, (1993), 3, No. 10, 2005–2010.

Derek R. Buckle et al. "Relaxant Activity of 4–Amido–3, 4–dihydro–2H–1–benzopyran–3–ols and 4–Amido–2H–1–benzopyrans on Guinea Pig Isolated Trachealis", *J. Med. Chem.*, (1990), 33, 3028–3034.

R. C. Small et al. "Potassium Channel Opening Drugs and the Airways", *Brazilian J Med Biol Res*, (1992) 25, 983–998.

*Primary Examiner*—Matthew V. Grumbling
*Attorney, Agent, or Firm*—Liza D. Hohenschutz

[57] ABSTRACT

Compounds of formula I

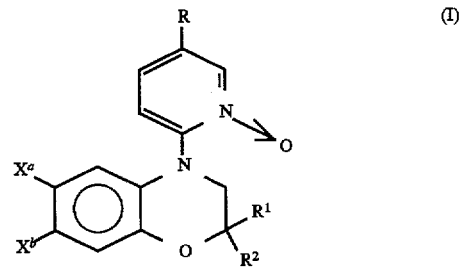

wherein $X^a$, $X^b$, R, $R^1$ and $R^2$ have any of the meanings given in the specification, and their pharmaceutically acceptable salts are useful as potassium channel openers for the treatment of urinary incontinence. Also disclosed are pharmaceutical compositions, processes for preparing the compounds of formula I and intermediates.

12 Claims, No Drawings

METHODS FOR USING BENZOXAZINES FOR TREATING ASTHMA

This is a continuation of application Ser. No. 08/239,637 filed on May 9, 1994, now U.S. Pat. No. 5,486,515.

This invention relates to a novel group of compounds which are potassium channel openers and are useful in the treatment of bladder instability in mammals such as man. More specifically, this invention relates to a group of benzoxazines, their use in the treatment of urinary incontinence in mammals (including man), processes for preparing them and pharmaceutical compositions containing them.

European patent applications publication numbers EP-A2-0432893 and EP-A1-500319 disclose certain benzoxazine derivatives having hydrogen atoms or alkyl groups at the 2-position which possess activity as potassium channel openers and are thereby capable of relaxing smooth muscle.

It is known that bladder tissue is excitable and that urinary incontinence can be caused by uncontrolled or unstable bladder contractions. Novel benzoxazines, having a fluoroalkyl substituent at the 2-position, have now been found that are unexpectedly capable of relaxing bladder smooth muscle, thus preventing or ameliorating uncontrolled or unstable bladder contractions. Hence, the compounds may be useful for the treatment of urge incontinence, which includes for example detrusor instability, which may result from cystitis, urethritis, tumors, stones, diverticuli or outflow obstruction; and detrusor hyperreflexia, which may result from stroke, dementia, parkinsons, suprasacral spinalcord injury or suprasacral spinalcord disease.

According to the invention there is provided a compound of formula I (formula set out, together with other formulae referred to by Roman Numerals, on pages following the Examples), or a pharmaceutically acceptable salt thereof, wherein R is hydrogen or trifluoromethyl $R^1$ and $R^2$ are independently selected from (1–3C)alkyl which may be substituted by one or more fluoro groups, provided that at least one of $R^1$ and $R^2$ is substituted by at least one fluoro group;

$X^a$ is selected from (A) cyano, nitro, trifluoromethyl, pentafluoroethyl, trifluoromethoxy, trifluoromethylsulfonyl, methylsulfonyl, halo, trifluoromethylthio, and (B) a group Y–Z connected to the benz ring through Z, wherein Y is a 6-membered aromatic ring or heteroaromatic ring containing 1–2 nitrogens as the heteroatoms and is connected to Z through carbon, and Z is selected from sulfonyl and carbonyl; and $X^b$ is selected from hydrogen, halogen, trifluoromethyl, trifluoromethylacetamido and (1–4C)alkoxy; or $X^a$ and $X^b$ together with the carbon atoms to which they are attached, form an 1-oxa-2,5-diazole, a 1-thia-2,5-diazole or a 1,2,5-triazole ring.

It will be appreciated that, when $R^1$ and $R^2$ are not defined as the same group, the compound of formula I may exist in, and be isolated in, optically-active forms. The compound may also exhibit polymorphism or form solvates. It is to be understood that the present invention encompasses any racemic, optically-active or polymorphic form, or solvate, or mixtures thereof, which form possesses potassium channel opening properties, it being well known in the art how to prepare optically-active forms (for example, by resolution of the racemic form or by synthesis from optically-active starting materials) and how to determine the potassium channel opening properties by the standard tests described hereinafter. It may be preferred to use the compound of formula I in a form which is characterized as containing, for example, at least 95%, 98% or 99% enantiomeric excess (ee) of the (S)-form as defined when $R^1$ is methyl and $R^2$ is trifluoromethyl.

The invention further provides a pharmaceutical composition suitable for the treatment of urinary incontinence, comprising a compound of formula I, or a pharmaceutically acceptable salt thereof, and a pharmaceutically acceptable diluent or carrier.

The invention further provides a method for the treatment of urinary incontinence, comprising administering to a mammal in need of such treatment an effective amount of a compound of formula I as defined above, or a pharmaceutically acceptable salt thereof.

In this specification the term "alkyl" includes both straight and branched chain radicals, but it is to be understood that references to individual radicals such as "propyl" embrace only the straight chain ("normal") radical, branched chain isomers such as "isopropyl" being referred to specifically.

Particular values from which $R^1$ and $R^2$ may independently be selected include methyl, ethyl, propyl, monofluoromethyl, difluoromethyl, trifluoromethyl, pentafluoroethyl, and heptafluoropropyl.

Particular values of 6-membered aromatic rings include phenyl.

Particular values of 6-membered heteroaromatic rings include 2-pyridyl, 3-pyridyl, 4-pyridyl, and 2-pyrimidinyl.

Preferred values from which $R^1$ and $R^2$ may be independently selected include methyl, monofluoromethyl, difluoromethyl, trifluoromethyl, ethyl, and pentafluoroethyl.

Preferred values of $X^a$ include 4-pyridylsulfonyl, 3-pyridylsulfonyl, phenylcarbonyl, 2-pyridylsulfonyl, 2-pyridylcarbonyl, cyano, nitro, trifluoromethyl, trifluoromethoxy, pentafluoroethyl, phenylsulfonyl, methylsulfonyl, trifluoromethylthio and trifluoromethylsulfonyl.

Particular values of $X^b$ include, hydrogen, chlorine, trifluoromethyl, trifluoromethylacetamido and methoxy. Preferably $X^b$ is hydrogen.

A particular value for Xa and Xb taken together with the carbon atom to which they are attached is 1-oxa-2,5-diazole.

A preferred group of compounds of formula I are those in which $R^1$ is methyl or ethyl and $R^2$ is trifluoromethyl; or in which $R^1$ and $R^2$ are each difluoromethyl.

The compound of Example 8 is especially preferred because of its potency in the first in vitro screen described hereinbelow.

Compounds of formula I can be made by processes which include processes known in the chemical arts for the production of structurally analogous compounds. Such processes for the manufacture of a compound of formula I as defined above are provided as further features of the invention and are illustrated by the following procedures in which the meanings of generic radicals are as given above unless otherwise qualified. A process for making a compound of formula I comprises (a) reacting a corresponding compound of formula II with a 2-halopyridine-1-oxide. The 2-halopyridine-1-oxide may be, for example, 2-chloro-pyridine-1-oxide. The reaction is preferably performed in the presence of a base, for example an alkali metal hydride such as sodium hydride. Suitable solvents include sulphoxides such as dimethyl sulfoxide. The reaction is conveniently performed at a temperature in the range of from 15° to 175 °C.

(b) oxidizing a corresponding pyridylbenzoxazine of formula III. For example, a pyridylbenzoxazine of formula III can be oxidized to the requisite pyridyl N-oxide with a perbenzoic acid such as m-chloroperbenzoic acid (MCPBA), conveniently in the presence of a radical inhibitor such as 3-t-butyl-4-hydroxy-5-methylphenyl sulfide (Y. Kishi et al., Chem. Comm., 1972, 64). The reaction may conveniently be performed at a temperature in the range of from 80° to 99° C. Suitable solvents include halogenated hydrocarbons such as ethylene dichloride. Magnesium monoperphthalate or oxone may also be employed as oxidizing agent, but MCPBA is preferred.

(c) for a compound of formula I wherein $X^a$ is YZ, Y is aryl or heteroaryl, and Z is sulfonyl, oxidizing a corresponding sulfide of formula IV. For example, a sulfide of formula IV can be oxidized to the corresponding (sulfonyl) compound of formula I with an alkali metal (e.g. potassium) permanganate in aqueous acetic acid at about 25°–50 °C. for about 1–3 hours, as generally known in the art.

(d) for a compound of formula I wherein $X^a$ is YZ, Y is aryl or heteroaryl, and Z is carbonyl, treating a compound of formula V, wherein $X^1$ is iodo or bromo, with an aluminum compound of formula $AlY_3$ and carbon monoxide in the presence of a suitable catalyst such as bis(acetonitrile) palladium dichloride. The reaction can be carried out in a suitable solvent such as DMSO or a mixture of tetrahydrofuran/DMPU and at a temperature in the range of from about 20° C. to about 100° C.

(e) for a compound of formula I wherein $X^a$ is YZ, Y is aryl or heteroaryl, and Z is carbonyl, treating a compound of formula V, wherein $X^1$ is iodo or bromo, with a tin compound of formula $SnY_4$, $Me_3SnY$, or $Bu_3SnY$ and carbon monoxide in the presence of a suitable catalyst such as tetrakis(triphenylphosphine)palladium. The reaction can be carried out in a suitable solvent such as tetrahydrofuran, DMSO, or DMPU and at a temperature in the range of from about 20° C. to about 100° C.

(f) for a compound of formula I wherein $X^a$ is cyano, treating a compound of formula V, wherein $X^1$ is iodo or bromo, with cuprous cyanide. The reaction can be conducted in a suitable solvent such as N,N-dimethylformamide, DMSO, or DMPU, and at a temperature of about 20° to about 200° C.

If not commercially available, the necessary starting materials for the above procedures may be made by procedures which are selected from standard organic chemical techniques, techniques which are analogous to the synthesis of known, structurally similar compounds, or techniques which are analogous to the above-described procedures or the procedures described in the examples.

In a preferred procedure, a benzoxazine of formula II wherein $X^a$ is other than cyano can be made by reducing the corresponding benzoxazinone of formula VI with a borohydride (Chem. Abstr. 111(1), 7384x), diborane (U.S. Pat. No. 4,766,118), or, preferably, with borane-dimethylsulfide complex (Hutchins et. al., Org. Prep. Proc. Int., 1981, 13(3–4), 225; brown et. al., Org. Chem., 1982, 47, 3153). This preferred method can be conducted in tetrahydrofuran at a temperature of about 50°–70° C. for a time of about 0.5 to about 3 hours.

Alternatively, a benzoxazine of formula II can be made by reductive cyclization of an aldehyde of formula IX, for example with hydrogen in the presence of Raney nickel. The reductive cyclization can be conducted in a solvent such as an alcohol (e.g. ethanol) and at a temperature of from about 0° C. to about 100° C.

A benzoxazine of formula II can also be made by (1) treating a nitro compound of formula XI with an alcohol of formula XII wherein $R^3$ is hydrogen, in the presence of a base such as sodium hydride, at a temperature in the range of about 0° C. to about 200° C., and in a solvent such as N,N-dimethylformamide, DMPU, DMSO, or tetrahydrofuran and, optionally, in the presence of copper catalyst such as copper iodide, or powdered or copper metal, thereby forming a corresponding aldehyde of formula XIII ($R^3$=H); followed by (2) conducting a reductive cyclization, for example with hydrogen in the presence of Raney nickel at a temperature of about 0° C. to about 100° C. in an alcohol solvent such as ethanol.

A compound of formula III may be prepared by reacting a compound of formula II with a 2-halopyridine such as 2-chloropyridine or 2-bromopyridine. A compound of formula V may be prepared in an analogous manner by reacting a coresponding compound of formula II, wherein $X^a$ is defined as $X^1$ with a 2-halopyridine-1-oxide.

A benzoxazinone of formula VI can be made by any of the following methods:

(a) cyclizing an amide of formula VII in which $X^3$ is fluorine or chlorine in the presence of a suitable catalyst such as an alkali metal fluoride (e.g potassium or cesium fluoride) or sodium hydride at a temperature generally in the range of about 100° C. to about 200° C. and in a suitable solvent such as N,N-dimethylformamide DMPU or DMSO;

(b) cyclizing a compound of formula VIII, wherein $R^5$ is alkyl (such as (1–3C)alkyl), by heating in a solvent such as N,N-dimethylformamide or tetrahydrofuran, optionally in the presence of a base such as potassium carbonate.

(c) (1) treating a nitro compound of formula XI, wherein $X^3$ is a suitable leaving group such as for example fluoro or chloro, with an alcohol of formula XII wherein $R^3$ is $NH_2$, in the presence of a base such as sodium hydride, at a temperature in the range of about 0° C. to about 200° C., and in a solvent such as N,N-dimethylformamide, DMPU, DMSO, or tetrahydrofuran and, optionally, in the presence of copper catalyst such as copper iodide, or powdered or copper metal, thereby forming a corresponding ether of formula XIII ($R^3$=$NH_2$); followed by (2) cyclizing in the presence of a base such as sodium hydride at a temperature of about 50°–200° C. The reaction can be conducted in a solvent such as N,N-dimethylformamide, DMSO, or DMPU;

(d) (1) treating a nitro compound of formula XI, wherein $X^3$ is a suitable leaving group such as for example fluoro or chloro, with an alcohol of formula XII wherein $R^3$ is $OR^4$ the group $R^4$ being selected from lower alkyl (e.g. (1–3C)alkyl such as methyl, ethyl, or propyl), benzyl and hydrogen, the reaction being conducted under conditions as described above in (c)(1) (and two equivalents of base being required if $R^4$ is H), thereby forming a corresponding ether of formula XIII ($R^3$=$OR^4$); followed by (2) conducting a reductive cyclization, for example with hydrogen in the presence of Raney nickel or palladium on carbon at a temperature of about 0° C. to about 100° C. in the presence of a solvent such as ethanol or tetrahydrofuran.

(e) treating a phenol of formula XIV with a compound of formula XV wherein $X^2$ is a leaving group such as chloro or triflate, in the presence of a suitable base such as an alkali metal carbonate or bicarbonate, or pyridine. The reaction can be conducted in a solvent such as methylisobutylketone at a temperature of from 20° C. to 100° C.

(f) for a compound in which $R^1$ and $R^2$ are both monofluoromethyl reacting a corresponding compound of formula VI in which $R^1$ and $R^2$ are both hydrogen with formaldehyde in the presence of a base, to afford the corresponding compound of formula VI in which $R^1$ and $R^2$ are both hydroxymethyl, and then reacting this compound with a fluorinating agent such as diethylaminosulphur trifluoride.

The compounds of formula VI may be prepared by reacting a compound of formula XVI, wherein $X^3$ is a suitable leaving group such as for example fluoro or chloro, with a compound of formula XII in which $R^3$ is $OR^4$ in the presence of an alkali metal fluoride such as cesium fluoride. Suitable solvents include amides such as dimethylformamide. The reaction is conveniently performed at a temperature in the range of from 0° to 100° C.

An anilide of formula VII can be made by coupling an aniline of formula XVI with an acid of formula XVII in the presence of a coupling agent such as thionyl chloride. The reaction can be conducted in a solvent such as DMA at a temperature of about −20° C. to about 25° C. The reaction can, alternatively, be conducted in tetrahydrofuran employing carbonyl as the coupling agent.

An aniline of formula XVI, wherein $X^3$ is a leaving group such as for example fluoro or chloro, can be made by reducing a corresponding nitro compound of formula XI with a suitable reducing agent such as tin chloride, in a solvent such as an alcohol (e.g. ethanol) and at a temperature of from about 20° C. to about 100° C.

A nitro compound of formula XI, in which $X^3$ is chlorine can be made by treating a nitro compound of formula XVIII with sulfuric acid and an alkali metal (e.g. sodium) nitrite in water as the solvent, followed by treating the product with cuprous chloride. Both treatment stages can be conducted at a temperature of from abut 20° C. to about 100° C.

A nitro compound of formula XI, in which $X^3$ is fluorine can be made by treating a nitro compound of formula XVIII with sulfuric acid and an alkali metal (e.g. sodium) nitrite in water as the solvent, followed by treating the product with fluoroboric acid. Isolation of the diazonium fluoroborate followed by heating gives the desired compound of formula XI.

Certain intermediates described hereinabove, for example, the compounds of formulae II and III, are novel and form further aspects of the invention.

It will be appreciated that some of the materials useful in synthesizing compounds according to the invention are readily commercially available and precedented in the chemical literature.

Examples of suitable pharmaceutically acceptable salts include acid addition salts formed with acids which form a physiologically acceptable anion, for example, anions derived from organic acids, such as tosylate, methanesulfonate, acetate, tartrate, citrate, succinate, benzoate, ascorbate, α-ketoglutarate, and α-glycerophosphate, and anions derived from inorganic acids, such as sulfate, nitrate and chloride. Pharmaceutically acceptable salts may be obtained using standard procedures well known in the art, for example by reacting a compound of formula I with a suitable acid affording a physiologically acceptable anion.

If a compound of formula I in an optically active form is desired, this may be obtained, for example, by synthesis starting from an optically active compound, or by a standard resolution of a compound of formula I in racemic or a less optically pure form.

When used to treat urinary incontinence, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a feature of the invention.

According to another aspect, therefore, the invention provides a pharmaceutical composition, which comprises a compound of formula I or a pharmaceutically acceptable salt thereof, as defined hereinabove, and a pharmaceutically acceptable diluent or carrier.

The compositions may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous, intravesicular, subcutaneous or intramuscular injection or infusion; or in the form of a patch for transdermal administration.

The invention further provides a method for the treatment of urinary incontinence, comprising administering to a mammal in need of such treatment an effective amount of a compound of formula I as defined above or a pharmaceutically acceptable salt thereof.

Treatment using a compound according to the invention can be remedial or therapeutic as by administering a compound following the onset or development of urinary incontinence in a patient. Treatment can also be prophylactic or prospective by administering a compound in anticipation that urinary incontinence may develop, for example in a patient who has suffered from incontinence in the past.

According to a further aspect, the invention provides the use of a compound of formula I, as defined hereinabove, in the manufacture of a medicament for the treatment of urinary incontinence.

It has also unexpectedly been found that compounds according to the invention are potassium channel openers. It is known that by functioning to open potassium channels, potassium channel opening compounds can thereby function to relax smooth muscle. While not wishing to be bound by theory, it is accordingly believed that the compounds of this invention function by opening potassium channels in bladder cells and thereby relax bladder smooth muscle tissue, thus preventing or ameliorating uncontrolled bladder contractions which can cause urinary incontinence.

Because compounds according to the invention function to open cell potassium channels, they may also be useful as therapeutic agents in the treatment of other conditions or diseases in which the action of a therapeutic agent which opens potassium channels is desired or is known to provide amelioration. Such conditions or diseases include hypertension, asthma, peripheral vascular disease, right heart failure, congestive heart failure, angina, ischemic heart disease, cerebrovascular disease, glaucoma, renal cholic, disorders associated with kidney stones, irritable bowel syndrome, male pattern baldness, premature labor, and peptic ulcers.

The dose of compound of formula I which is administered will necessarily be varied according to principles well known in the art taking account of the route of administration, the severity of the incontinence condition, and the size and age of the patient. In general, a compound of formula I will be administered to a warm blooded animal (such as man) so that an effective dose is received, generally a daily dose of above 0.005, for example in the range of about 0.01 to about 10 mg/kg body weight. Preferably the compound is administered orally in this dose range.

It will be apparent to those skilled in the art that a compound of formula I can be co-administered with other therapeutic or prophylactic agents and/or medicaments that are not medically incompatible therewith. Compounds within the scope of the invention have not been found show any indication of untoward side-effects in laboratory test animals at several multiples of the minimum effective dose.

The actions of compounds of formula I as smooth muscle relaxants useful as therapeutic agents for the treatment of urinary incontinence through their action to open potassium channels and hyperpolarize the membrane potential in the bladder detrusor smooth muscle can be shown using suitably designed in vitro tests, such as the one described following. Compounds according to the invention have been found to be active at 30 µM (micromolar) or less in this test. Compounds exemplified herein have typically been found to exhibit an $IC_{50}$ on the order of 30 micromolar or less in the test. For example, the compound described in Example 1 exhibits an $IC_{50}$ of 0.54 micromolar in the test. "$IC_{50}$" is a well understood term and means the concentration of test compound which causes a 50% decrease in the in vitro contraction of the bladder tissue described in the following test.

Male albino Hartley guinea pigs (450–500g) are sacrificed by carbon dioxide induced asphyxiation and quickly exsanguinated. The lower abdominal cavity is opened and the urinary bladder isolated. The bladder is cleaned of surrounding connective and adipose tissue, and the portion above the ureteral orifices is removed and washed in Krebs-Henseleit buffer solution of the following composition (in mM): NaCl 118.0, KCl 4.7, $MgSO_4$ 1.2, $KH_2PO_4$ 1.2, $CaCl_2$ 2.5, $NaHCO_3$ 25.0 and d-glucose 11.1. The solution is warmed to 37° C. and gassed with 95% $O_2$ and 5% $CO_2$. With vigorous bubbling, the solution should have a pH value close to 7.4.

The dome of the washed bladder is cut off and discarded; the remaining bladder is placed on a gauze in a Petri dish containing the buffer solution. A mid-ventral longitudinal cut is made with scissors to open the bladder. The strips cut from the dome and the base edge are discarded. The remaining detrusor mid-section is cut into two horizontal strips with an approximate width of 2.0 mm. These two strips are further bisected at the mid-dorsal section, creating four strip of similar dimensions. Each strip thus contains both dorsal and ventral portions of the bladder.

The two ends of each individual strip are tied to a glass support rod and a force-displacement transducer (Grass model FR03), respectively, with 4–0 black braided silk suture.

The transducers are connected to a polygraph (Grass model 7E), which is calibrated at 5 mV/cm and the calibration checked for linearity with weights of 5 and 0.5 grams. The analog electrical output signals from the polygraph are digitized by a Modular Instrument Micro 5000 signal processing system using Biowindow Data Acquisition Software, which is run under the Microsoft OS/2 operating system with an IBM-compatible PC.

The detrusor strips on the glass rod are secured in 20 ml tissue baths and allowed to equilibrate under a preload tension of 2 grams. During the following 45 to 60 min equilibration period, the tissue is washed with fresh buffer solution at 15 min interval, with the tension adjusted if necessary, to 2 grams prior to washing. After the equilibration period, a priming dose of 15 mM KCl (total concentration in the bath) is applied. The tissue is washed after 10 min and washed twice more at 15 min intervals with tension adjusted to 2 grams before each washing.

When the tissue relaxes to a steady state after the final washing, 15 mM KCl is again applied. Once the myogenic activity of the tissue reaches a steady state, the baseline data are acquired through the Biowindows Data Acquisition System by averaging 5 min of the myogenic data sampled at 32 Hz. Once the baseline is acquired, the experimental compounds are dosed in a cumulative manner in half log unit increments. The contact time for each dose is 10 min with the final 5 min being the period of time that the dose reponse data are required. If 30 µM of the test compound does not abolished the detrusor mechanical activity, then 30 µM cromakalim, a putative potassium channel opener, is dosed to establish a maximum response. The effect of the compound at each dose is expressed as % of the maximum inhibitory response, which is further normalized with respect to the corresponding effect of the compound vehicle control. The normalized response is then used to derive the $IC_{50}$ of the relaxant activity of the compound through the application of Marquardt's nonlinear iterative curve fitting technique to a standard dose-response function.

The following data is a comparison of the ability to relax bladder smooth muscle for compounds of the invention and their non-fluorinated analogs as measured in the above described in vitro test:

| Xa | Xb | R | $R^1$ | $R^2$ | IC50 (uM) | Example |
|---|---|---|---|---|---|---|
| $PhSO^2$ | H | H | $CH_3$ | $CH_3$ | 4.1 | * |
| $PhSO^2$ | H | H | $CH_2F$ | $CH_2F$ | 2.25 | 5 |
| $PhSO^2$ | H | H | $CH_3$ | $CF_3$ | 0.54 | 1 |
| $PhSO^2$ | H | H | $CHF_2$ | $CHF_2$ | 0.36 | 6 |
| $NO_2$ | H | H | $CH_3$ | $CH_3$ | 0.074 | @ |
| $NO_2$ | H | H | $CH_2F$ | $CH_2F$ | 0.025 | 4 |
| $NO_2$ | H | H | $CHF_2$ | $CHF_2$ | 0.007 | 8 |

*Exampie 3 at page 25 of EP 0 432 893
@Example 1 at pages 22–23 of EP 0 432 893

Compounds of the invention demonstrate a clear and unexpected advantage over their closest related non-fluorinated analog.

The ability of compounds according to the invention to open potassium channels in detrusor smooth muscle can be further demonstrated by a second in vitro test. This second in vitro test is similar to the one described above with regard to tissue preparation and data acquisition. However, the following exceptions are noted. In this second test, the contraction of the detrusor strips during priming and after the equilibration period is achieved with 80 mM instead of 15 mM KCl (total concentration in the bath). A sustained tension in the tissue is evident after this high KCl stimulation, because voltage-sensitive calcium channels have been rendered open to permit an influx of calcium into the cells and the development of tonic tension. This tension is totally abolished with 300 µM of papaverine, which is thereby used to establish the maximum response in this test.

Typical calcium channel blockers like nifedipine, nimodipine, isradipine, and verapamil are able to relax and reduce the myogenic activity of guinea pig detrusor strips in both tests by virtue of their blocking action on calcium channels. However, all of the aforementioned calcium channel blockers are more potent in the second test when 80 mM KCl is used, than in the first test where 15 mM KCl is used. In contrast, while the putative potassium channel opener cromakalim has a potent relaxant activity in the first test with an $IC_{50}$ in the range of 0.6 to 0.9 µM, it demonstrates insignificant relaxant activity in the second test at concentrations as high as 30 µM. Thus, the profile of a higher relaxant activity in the first test than in the second of compounds according to the invention indicates that the compounds are functioning as potassium channel openers.

The ability of the compounds according to the invention to act as potassium channel openers on bladder tissue may be further demonstrated by a standard test which measures the effect of test compounds on the rate of efflux of rubidium ($^{86}Rb$) or potassium ($^{42}K$) from the tissue.

The invention will now be illustrated by the following non-limiting examples in which, unless stated otherwise:

(i) temperatures are given in degrees Celsius (C); operations were carried out at room or ambient temperature, that is, at a temperature in the range of 18°–25°;

(ii) evaporation of solvent was carried out using a rotary evaporator under reduced pressure (600–4000 pascals; 4.5–30 mm Hg) with a bath temperature of up to 60°;

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm silica gel GHLF plates (Art 21521), obtainable from Analtech, Newark, Del., USA;

(iv) in general, the course of reactions was followed by TLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only;

(viii) reduced pressures are given as absolute pressures in pascals (Pa); other pressures are given as gauge pressures in bars;

(ix) chemical symbols have their usual meanings; the following abbreviations have also been used: v (volume), w (weight); mp (melting point), L [liter(s)], mL (milliliters), mM (millimoles), g [gram(s)], mg [milligram(s)], min (minutes), h (hour); and (x) solvent ratios are given in volume:volume (v/v) terms.

(xi) conventional acronyms have been used for convenience, including tetrahydrofuran, DMSO (dimethylsulfoxide), N,N-dimethylformamide, DMPU (N,N'-dimethylpropyleneurea), DMA (dimethylacetamide), CDI (carbonyldiimidazole).

EXAMPLE 1

2-(2-Methyl-2-trifluoromethyl-6-phenylsulfonyl-3,4-dihydro-2H-1,4-benzoxazin-4-yl)pyridine-N-oxide.

A solution of 2-methyl-2-trifluoromethyl-6-phenylsulfonyl-3,4-dihydro-2H-1,4-benzoxazine (200 mg) and 2-chloropyridine N-oxide·HCl (121 mg;) in dimethylsulfoxide (8 mL) was treated with sodium hydride (60% dispersion in oil, 58 mg), and stirred under a nitrogen atmosphere for 18 hours. The mixture was then poured into a solution containing aqueous sodium hydroxide (0.5 N, 150 mL) and saturated sodium chloride (20 mL.) and extracted with ethyl acetate. (3×150 mL). The combined organic portions were washed with aqueous sodium hydroxide (0.5 N, 30 mL) and saturated sodium chloride (5 mL) and evaporated to yield a black semi-solid. Chromatography of this solid on silica gel eluting with ethyl acetate then ethyl acetate/methanol (97:3) yielded the title compound (110 mg) as a white solid; mp 192°–193° C.; NMR (250 MHz, d6-DMSO): 1.55 (s,3), 3.98 (dd,2), 6.8.1 (s,1), 7.20 (d,1), 7.40 (dd, 1), 7.45 (m,2), 7.62 (m,4) 7.85 (dd,2), 8.42 (d, 1); MS: m/z=451(M+1). Analysis for $C_{21}H_{17}F_3N_2O_4S$: Calculated: C, 56.00; H, 3.78; N, 6.22; Found: C, 56.10; H, 3.88; N, 6.02.

The 2-Methyl-2-trifluoromethyl-6-phenylsulfonyl-3,4-dihydro-2H-1,4-benzoxazine starting material was obtained as follows:

a. 2-Nitro-4-(phenylsulfonyl)chlorobenzene. Sodium nitrite (2.73 g), was added portionwise to concentrated sulfuric acid (50 mL) over a period of 10 minutes; heated to 70° C. to give a homogeneous solution, then cooled to room temperature. A suspension containing 2-nitro-4-phenylsulfonylaniline (10 g), prepared essentially as reported in Example 4 of U.S. Pat. No. 3,796,710, in glacial acetic acid (75 mL) was added to the sodium nitrite solution maintaining the internal temperature below 40° C. during the addition. The reaction temperature was maintained at 40° C. for 1 hour. The solution was poured into a solution containing cuprous chloride (7.48 g) in concentrated hydrochloric acid (75 mL) and heated to 80° C. for 1.0 hour. Water (500 mL) was added, then the reaction mixture was cooled to 0° C. and stirred for 1.0 hour. A pale yellow solid was collected by vacuum filtration and washed (water) (3×50 mL). The solid was extracted with dichloromethane (3×150 mL), dried over magnesium sulfate, filtered, and solvent removed under vacuum yielding the chloride (10 g) as a pale orange-yellow solid; mp 118°–120° C.; NMR: 7.71 (M,3), 7.76 (d,1); 8.04 (m,3), 8.26 (dd,3), 8.67 (d,1) MS: m/z=298 (M+1).

b. 2-Methyl-2-(2-nitro-4-phenylsulfonylphenoxy)-3,3,3-trifluoropropanoic acid. To a cooled suspension (0° C.) containing sodium hydride (60% dispersion in oil, 2.36 g), in dimethylformamide (120 mL) was added 2-hydroxy-2-trifluoromethylpropanoic acid (4.46 g) portionwise. The mixture was allowed to warm to room temperature and stirred for 30 minutes. The mixture was cooled to 0° C., and 2-nitro-4-(phenylsulfonyl)chlorobenzene (7.0 g) was added in one portion. The mixture was stirred at room temperature for 18 hours then poured into aqueous HCl (1N, 1.0 L) and extracted with ethyl acetate. The combined organic portions were washed (brine) and evaporated to yield a black semi-solid. Chromatography, eluting with dichloromethane, then dichloromethane:methanol (95:5), yielded the ether (9.86 g) as a pale brown oil: MS: m/z=420(M+1); NMR: 1.81 (s,3), 7.41 (d,1), 7.72 (m,3), 7.95 (s,1,), 8.03 (m,2), 8.16 (dd, 1).

c. 2-Methyl-2-(2-amino-4-phenylsulfonylphenoxY)-3,3,3-trifluoropropanoic acid. To a solution of the ether of step b. (2.65 g) in tetrahydrofuran (150 mL) was added palladium on carbon (10%, 0.88 g). The mixture was placed under a hydrogen atmosphere (15 p.s.i.g) for 3 hours. The catalyst was then removed by vacuum filtration through a celite pad. The solvent was evaporated yielding the aniline (2.46 g) as an oil: MS: m/z=388(M+1); 250 MHz NMR: 1.78 (s,3), 7.32 (d,1), 7.68 (m,5), 7.96 (d,2), 11.67 (broad s,1).

d. 2-Methyl-2-trifluoromethyl-3-oxo-6-phenylsulfonyl-3,4-dihydro-2H-1,4-benzoxazine. To a solution containing 4-dimethylaminopyridine (0.31 g) in tetrahydrofuran (25 mL) cooled to −30 ° C. was added thionyl chloride (131 mg). The mixture was stirred for 15 minutes. The aniline of step c. (0.42 g) was added and reaction mixture was stirred for 18 hours then poured into aqueous HCl (1N, 100 mL) and extracted with ethyl acetate. The combined ethyl acetate extracts were washed (brine) and evaporated. Chromatography, eluting with hexane:ethyl acetate (3:1) yielded the benzoxazinone (0.26 g) as a white solid; mp 184°–186° C.; MS: m/z=372(M+1); 250 MHz NMR: 1.63 (s,3), 7.13 (1), 7.70 (d,1), 7.88 (dd,1), 11.08 (broad s, 1).

e. 2-Methyl-2-trifluoromethyl-6-phenylsulfonyl-3,4-dihydro-2H-1,4-benzoxazine. A solution of the benzoxazinone of step d. (0.374 g) in tetrahydrofuran (12 mL) was treated with borane-methyl sulfide complex (10M, 1.81 mL) and then heated to 70° C. for 2 hours. Excess borane was quenched by the addition of methanol. The solvent was evaporated and the resulting residue was chromatographed, eluting with hexane:ethyl acetate (7:2) to provide the benzoxazine (0.33 g) as a white solid; mp 138°–139° C.; MS: m/z=358(M+1); 250 MHz NMR: 1.42 (s,3), 3.34 (m,2), 6.68 (broad s), 6.98 (d,1), 7.14 (dd,1), 7.83 (m,3): Analysis for $C_{16}H_{14}F_3NO_3S$: Calculated: C, 53.78; H, 3.92; N, 3.92; Found: C, 53.78; H, 3.95; N, 3.91.

An alternative synthesis of the intermediate of step d. is as follows;

f. 3-Phenylsulfonyl-6-chloroaniline. 2-Nitro-4-(phenylsulfonyl)-chlorobenzene (9.8 g) and stannous chloride dihydrate (33.5 g) were suspended in absolute ethanol (200 mL) and heated to 75° C. for 40 minutes. The solvent was then removed under vacuum. The residue was cooled to 0° C., water (100 mL) was added, and enough aqueous sodium hydroxide (2.0N) was added to give a pH of 8.0. The tin salts were then removed by filtration. The filtered aqueous solution was extracted with ethyl acetate (4×200 mL) and the solvent was removed under vacuum leaving a brown solid. Chromatography over silica gel, eluting with dichloromethane yielded the aniline (7.3 g) as an orange solid; mp 105°–107° C.; NMR: 5.96 (s,2), 7.02 (dd,1), 7.34 (d,1) 7.41 (d,1) 7.61 (m,3), 7.88 (d,2); MS: m/z=268(M+1).

g. N-(2-Chloro-5-phenylsulfonylphenyl)-3,3,3-trifluoro-2-hydroxy-2-methylpropanamide. To a solution containing 2-hydroxy-2-methyl-3,3,3-trifluoropropanoic acid (2.00 g) in dimethylacetamide (40 mL) cooled to −20° C. was added thionyl chloride (1.50 g) and the mixture was stirred under a nitrogen atmosphere for 1.0 hour. 3-Phenyl-sulfonyl-6-chloroanilin (2.42 g) was added in one portion and the mixture was stirred for 48 hours at room temperature. The reaction mixture was then poured into aqueous sodium hydroxide (1.0N, 250 mL) and extracted with ethyl acetate (3×150 mL). The ethyl acetate extracts were combined, washed with aqueous sodium hydroxide (2.0N, 2×50 mL) then with saturated brine (50 mL) and the solvent was then removed under vacuum. Chromatography over silica gel eluting with hexane/ethyl acetate (first 4:1 and then 2:1) yielded the amide (1.25 g) as a white solid; mp 79°–80° C.; NMR: 1.61 (s,3), 7.69 (m,3), 7.82 (m,2), 7.94 (d,1), 7.98 (m,2), 8.52 (s,1), 9.93 (s,1); MS: m/z=408(M+1). Analysis for $C_{16}H_{13}NO_4SClF_3$: Calculated: C, 47.11; H, 3.19; N, 3.44; Found: C, 47.10; H, 3.28; N, 3.38.

h. 2-Methyl-2-trifluoromethyl-3-oxo-6-phenylsulfonyl-3,4-dihydro-2H-1,4-benzoxazine. A suspension of N-(2-Chloro-5-phenylsulfonylphenyl)-3,3,3-trifluoro-2-hydroxy-2-methylpropanamide (1.64 g) and potassium fluoride (1.05 g) in dry N,N-dimethylformamide (35 mL) was refluxed under nitrogen for 6.0 days. The mixture was cooled to room temperature, poured into an aqueous solution containing brine (450 mL) and aqueous sodium hydroxide (6N, 25 mL) and extracted with ethyl acetate (3×250 mL). The combined ethyl acetate extracts were washed with saturated brine (2×50 mL). The solvent was removed under vacuum yielding a black oil which was chromatagraphed over silica gel, eluting with hexane:ethyl acetate (first 3:1 and then 1:1), to yield the benzoxazine (0.26 g) as a white solid; mp 184–186° C.; NMR: 1.63 (s,3), 7.13 (d,1), 7.70 (d,1), 7.88 (dd,1), 11.08 (broad s,1); MS: m/z=372(M+1).

EXAMPLE 2

S-(+)-2-(2-Methyl-2-trifluoromethyl-6-phenylsulfonyl-3,4-dihydro-2H-1,4-benzoxazine-4-yl)pyridine-N-oxide.

A solution of S-(+)-2-methyl-2-trifluoromethyl-6-phenylsulfonyl-3,4-dihydro-2H-1,4-benzoxazine (2.5 g) and 2-chloropyridine-N-oxide·HCl (1.51 g) in dimethylsulfoxide (50 mL) was treated with sodium hydride (60% dispersion in oil, 0.73 g) and stirred for 18 hours. The mixture was heated to 50° C. for 5 hours then cooled to room temperature. The mixture was then poured into a solution containing aqueous sodium hydroxide (1N, 500 mL) and saturated brine (400 mL) and extracted with ethyl acetate. The combined organic portions were washed with a solution containing aqueous sodium hydroxide (1.0N, 30 mL) and saturated brine (40 mL) and evaporated to yield a black semi-solid. Chromatography, eluting with ethyl acetate then ethyl acetate/methanol (97:3), yielded the title compound (2.3 g) as a white solid; mp 188°–189 ° C.; $[\alpha]_D^{23}$=+39.05°; MS: m/z=451(M+1); 250 MHz NMR: 1.55 (s,3), 3.98 (dd,2), 6.81 (s,1), 7.20 (d,1), 7.40 (dd,1), 7.45 (m,2), 7.62 (m,4), 8.42 (d,1). Analysis for $C_{21}H_{17}F_3N_2O_4S$: Calculated: C, 56.00; H, 3.78; N, 6.22; Found: C, 56.05; H, 3.64; N, 6.14.

The necessary starting material was prepared from (S)-(−)-3,3,3-trifluoro-2-hydroxy-2-methylpropionic acid (preparation described in EP-A1-524781) following the method of Example 1 above, steps a. to e.

EXAMPLE 3

R-(−)-2-(2-Methyl-2-trifluoromethyl-6-phenylsulfonyl-3,4-dihydro-2H-1,4-benzoxazine-4-yl)pyridine-N-oxide.

A solution of R-(−)-2-methyl-2-trifluoromethyl-6-phenylsulfonyl-3,4-dihydro-2H-1,4-benzoxazine (800 mg) and 2-chloropyridine-N-oxide-HCl (447 mg) in dimethylsulfoxide (25 mL) was treated with sodium hydride (60% dispersion in oil, 220 mg) and stirred for 48 hours. The black mixture was poured into a solution containing aqueous sodium hydroxide (1N, 150 mL) and saturated brine (100 mL) and extracted with ethyl acetate. The combined organic portions were washed with a solution containing aqueous sodium hydroxide (1N, 35 mL and saturated brine (35 mL) and evaporated to yield a black semi-solid. Chromatography, eluting with ethyl acetate then ethyl acetate:methanol (97:3), yielded the title compound (620 mg) as a white solid; mp 188°–189 ° C.; $[\alpha]_D$=−39 (ethyl acetate); MS: m/z=451(M=1); NMR: 1.55 (s,3), 3.98 (dd,2), 6.81 (s,1), 7.20 (d,1), 7.40 (dd,1), 7.45 (m,2), 7.62 (m,4)

The starting material R-(−)-2-methyl-2-trifluoromethyl-6-phenylsulfonyl-3,4-dihydro-2H-1,4-benzoxazine was prepared as follows:

(R)-(−)-3,3,3-Trifluoro-2-hydroxy-2-methylpropanoic acid (prepared by a method analogous to that used to prepare the (S)-isomer described in EP-A1-524781) was subjected to a procedure similar to that described in Example 1.a.–1.e. to give the desired R-(−)-2-methyl-2-trifluoromethyl-6-phenylsulfonyl-3,4-dihydro-2H-1,4-benzoxazine.

EXAMPLE 4

2-(2,2-(bis)Fluoromethyl-6-nitro-3,4-dihydro-2H-1,4-benzoxazine-4-yl)pyridine-N-oxide.

A solution of 2,2-(bis)fluoromethyl-6-nitro-3,4-dihydro-2H-1,4-benzoxazine (1.33 g) and 2-chloropyridine N-oxide-HCl (1.15 g) in dimethylsulfoxide (35 mL) was treated with sodium hydride (60% dispersion in oil, 0.56 g). After 18 hours, the reaction was poured into aqueous sodium hydroxide (0.1N, 800 mL) and extracted with ethyl acetate. The combined organic portions were washed (brine) and evaporated to yield a black semi-solid. Chromatography, eluting with dichloromethane then dichloromethane:methanol (96:4), yielded the title compound (0.97 g) as a brown solid;

mp 162°–163 °C.; MS: m/z=338(M+1); NMR: 3.94 (s,2), 4.65 (s,2), 4.84 (s,2), 8.97 (d,1), 8.41 (d,1). Analysis for $C_{15}H_{13}F_2N_3O_4$: Calculated: C, 53.41; H, 3.86; N, 12.46; Found: C, 53.34; H, 4.03; N, 11.98.

The starting 2,2-(bis)Fluoromethyl-6-nitro-3,4-dihydro-2H-1,4-benzoxazine was obtained as follows:

a. 3-Oxo-6-nitro-3,4-dihydro-2H-1,4-benzoxazine. A solution of 2-amino-4-nitrophenol (8.80 g), in methyl isobutyl ketone (30 mL) was treated with sodium bicarbonate (11.5 g) and distilled water (35 mL). The mixture was cooled to 5° C. under a nitrogen atmosphere, treated dropwise with chloroacetyl chloride (5.0 mL) and then heated to reflux for 18 hours. A brown solid was collected from the cooled mixture by filtration. The solid was dried under vacuum at 50° C. for 24 hours yielding benzoxazinone (10.5 g) as a brown solid; mp 235°–236° C.; MS: m/z=195(M+1); NMR: 4.76 (s,2), 7.14 (d,1), 7.74 (d,1), 7.82 (dd,1), 11.07 (broad s,1).

b. 2,2-(bis)Hydroxymethyl-6-nitro-3-oxo-3,4-dihydro-2H-1,4-benzoxazine. A solution of the product of step a. (5.5 g), aqueous formaldehyde (37%, 11.55 mL) and aqueous sodium hydroxide (1H, 3.5 mmol) was heated to 120° C. under nitrogen atmosphere for 3.0 hours. The solvent was evaporated yielding a brown oil. Chromatography, eluting with dichloromethane:methanol (95:5), yielded the bis-alcohol (4.55 g) as a pale yellow solid; mp 205°–206° C.; MS: m/z=255(M+1); NMR: 3.54 (dd,2), 3.82 (dd,2), 5.26 (t,2), 7.06 (d,1), 7.66 (d,1), 7.80 (dd,1), 11.01 (s,1). Analysis for $C_{10}H_{10}N_2O_6$: Calculated: C, 47.24; H, 3.94; N, 11.02; Found: C, 47.37; H, 4.08; N, 10.97.

c. 2,2-(bis)Fluoromethyl-6-nitro-3-oxo-3,4-dihydro-2H-1,4-benzoxazine. To a cooled solution (5° C.) containing diethylaminosulfur trifluoride (2.84 g) in tetrahydrofuran (45 mL) was added, dropwise, a solution of the product of step b. (2.03 g) in tetrahydrofuran (70 mL). The mixture was stirred at 5° C. for 15 minutes and at room temperature for 18 hours. The plum-colored solution was then poured into brine and extracted with ethyl acetate. The combined organic extracts were washed (brine) and evaporated. Chromatography, eluting with dichloromethane then dichloromethane:methanol (98:2), yielded the bis-fluoro compound (1.60 g) as a pale yellow solid; MS: m/z=259(M+1); NMR: 4.65 (d,1), 4.89 (dd,2), 5.07 (d,1), 7.24 (d,1), 7.75 (d,1), 7.88 (dd,1), 11.58 (broad s,1 ).

d. 2,2-(bis)Fluoromethyl-6-nitro-3,4-dihydro-2H-1,4-benzoxazine. A solution of the product of step c.(1.69 g) in tetrahydrofuran (65 mL) was treated with borane-methyl sulfide complex (10M, 11.8 mL) and then heated to 70° C. for 3 hours. Excess borane was quenched by the addition of methanol. The solvent was evaporated and the resulting residue was chromatographed, eluting with dichloromethane:hexane (2:1), to provide 2,2-(bis)Fluoromethyl-6-nitro-3,4-dihydro-2H-1,4-benzoxazine (1.53 g) as a yellow-orange solid; mp 139°–141 ° C.; MS: m/z=245(M+1); NMR: 3.31 (s,2), 4.50 (m, 2), 4.69 (d,1), 6.64 (broad s,1), 6.98 (d,1), 7.47 (dd,1), 7.56 (d,1). Analysis for $C_{10}H_{10}F_2N_2O_3$: Calculated: C, 49.18; H, 4.10; N, 11.48; Found: C, 49.20; H, 4.20; N, 11.44.

EXAMPLE 5

2-(2,2-(bis)Fluoromethyl-6-phenylsulfonyl-3,4-dihydro-2H-1,4-benzoxazine-4-yl)pyridine-N-oxide.

A solution of 2,2-(bis)fluoromethyl-6-phenylsulfonyl-3,4-dihydro-2H-1,4-benzoxazine (5.50 g) and 2-chloropyridine N-oxide-HCl (3.10 g), in dimethylsulfoxide (150 mL) was treated with sodium hydride (60% dispersion in oil, 1.47 g), and stirred for 15 minutes then heated to 80° C. for 18 hours. The solvent was then evaporated and the residue was poured into a solution containing saturated brine (500 mL) and aqueous sodium hydroxide (2N, 200 mL) and extracted with ethyl acetate. The combined organic extracts were washed with saturated brine (50 mL) and aqueous sodium hydroxide (2N, 20 mL) and evaporated yielding a black residue. Chromatography, eluting with ethyl acetate, yielded a solid. Crystallization from ethyl acetate, yielded the title compound (3.19 g) as a pale tan solid; mp 190°–191° C.; MS: m/z=433(M+1); NMR: 3.88 (s,2), 4.60 (m,2), 4.76 (m,2), 6.73 (d, 1), 7.16 (d,1), 7.38 (m, 2), 7.47 (m,1), 7.64 (m,1), 7.83 (m,2), 8.40 (m,1). Analysis for $C_{21}H_{18}F_2N_2O_4S$: Calculated: C, 58.33; H, 4.20; N, 6.48; Found: C, 58.31; H, 4.40; N, 6.20.

The starting 2,2-(bis)Fluoromethyl-6-phenylsulfonyl-3,4-dihydro-2H-1,4-benzoxazine was obtained as follows:

a. 2-Nitro-4-phenylsulfonylphenol. A solution containing nitric acid (70%, 8.95 g) in glacial acetic acid (45 mL) was added in one portion to a solution containing 4-phenylsulfonylphenol (9.35 g) in glacial acetic acid (150 mL) and stirred for 18 hours. The yellow solution was poured into ice water (1200 mL) and stirred for 30 minutes. The yellow precipitate was collected by vacuum filtration and washed (water) yielding the nitro compound (11.15 g) as a pale yellow solid; MS: m/z=280(M+1); NMR: 7.22 (d,1), 7.64 (m,3), 7.96 (m,3), 8.39 (d,1), 11.26 (s, 1).

b. 2-Amino-4-phenylsulfonylphenol. To a solution containing 2-nitro-4-phenylsulfonylphenol (11.15 g) in methanol (700 mL) was added palladium on carbon (10%, 1.25 g). The resultant suspension was placed under hydrogen (3 atmospheres) for one hour. The catalyst was then removed by vacuum filtration through a celite pad. The filtrate was evaporated yielding a black residue which was chromatographed, eluting with ethyl acetate:hexane (1:1) to give the aniline (8.5 g) as an orange solid; mp 164°–165 ° C.; MS: m/z=250(M+1); NMR: 5.07 (broad s,2), 6.78 (d,1), 7.01 (dd,1), 7.10 (d,1), 7.60 (m,3), 7.82 (m,2), 10.26 (broad s).

c. 3-Oxo-6-phenylsulfonyl-3,4-dihydro-2H-1,4-benzoxazine. Using a procedure similar to that described in Example 4. a., except using 2-amino-4-phenylsulfonylphenol (7.45 g) and chloracetyl chloride (2.74 mL) the benzoxazinone (8.39 g) was prepared as a pale tan solid; mp 220°–222 ° C.; MS: m/z=290(M+1); NMR: 4.69 (s,2), 7.13 (d,1), 7.44 (d,1), 7.51 (dd,1), 7.65 (m,3), 7.90 (m,2), 10.93 (broad s,1).

d. 2,2-(bis)Hydroxymethyl-3-oxo-6-phenylsulfonyl-3,4-dihydro-2H-1,4-benzoxazine. Using a procedure similar to that described in Example 4. b., but using the product of step c. (8.35 g) and aqueous formaldehyde (37%, 16.35 mL) the bis-alcohol (7.51 g) was obtained as a white solid; mp 203°–205 ° C.; MS: m/z=350(M+1); NMR: 3.49 (dd,2), 3.77 (dd,2), 5.17 (t,2), 7.04 (d,1), 7.33 (d,1), 7.45 (dd,1), 7.66 (m,3), 7.87 (m,2), 10.84 (broad s,1).

e. 2,2-(bis)Fluoromethyl-3-oxo-6-phenylsulfonyl-3,4-dihydro-2H-1,4-benzoxazine. Using a procedure similar to that described in Example 4. c., but using the product of step d.(7.5 g) and diethylaminosulfur trifluoride (9.09 mL) the bis-fluoride (6.34 g) was obtained as a brown foam: MS: m/z=354(M+1); NMR: 4.62 (d,1), 4.78 (d,1), 4.86 (d,1), 5.02 (d,1), 7.22 (d,1), 7.45 (d,1), 7.54 (dd,1), 7.65 (m,3), 7.92 (m,2), 11.42 (s,1).

f. 2,2-(bis)Fluoromethyl-6-phenylsulfonyl-3,4-dihydro-2H-1,4-benzoxazine. Using a procedure similar to that described in Example 4. d., but using the product of step e. (6.31 g) and borane-methylsulfide complex (10M, 28.6 mL), 2,2-(bis)Fluoromethyl-6-phenylsulfonyl-3,4-dihydro-2H-1, 4-benzoxazine (5.57 g) was obtained as a white solid; MS: m/z=340(M+1); NMR: 3.52 (s,2), 4.47 (m, 2), 4.63 (m,2), 6.50 (broad s), 6.96 (d,1), 7.13 (dd,1), 7.24 (d,1), 7.63 (m,3), 7.88 (m,2).

EXAMPLE 6

2-(2,2-bis(Difluoromethyl)-6-phenylsulfonyl-3,4-dihydro-2H-1,4-benzoxazine-4-yl)pyridine-N-oxide.

A solution of 2-(2,2-bis(difluoromethyl)-6-phenylsulphonyl-3,4-dihydro-2H,1,4-benzoxazine-4-yl) pyridine (0.175 g), m-chloroperbenzoic acid (0.104 g), 3-tert-butyl-4-hydroxy-5-methylphenyl sulfide (0.0215 g), and 1,2-dichloroethane (10 mL) was refluxed under a nitrogen atmosphere for 18 hours. The cooled mixture was diluted with dichloromethane and extracted (saturated sodium, bicarbonate solution, water, brine), dried, and evaporated. Chromatography, eluting with ether, then methanol, followed by crystallization from warm ethyl acetate/hexanes gave the title compound as an off-white solid (0.087 g); mp 186°–190 ° C.; NMR: 4.07 (s,2), 6.56 (t,2), 6.88 (s,1), 7.28 (d,1), 7.38 to 7.68 (m,7), 7,84 (d,2), 8.41 (d,1); MS: m/z=469(M+1). Analysis for $C_{21}H_{16}F_4N_2O_4S$: Calculated: C, 53.85; H, 3.44; N, 5.98; Found: C, 53.52; H, 3.63; N, 5.60.

a. 2,2-bis(Difluoromethyl)-6-amino-3,4-dihydro-2H-1,4-benzoxazin-3-one. A solution of the product of Example 8.b. (14.7 g) in ethyl acetate (200 mL) was hydrogenated in the presence of 10% Pd/C. The catalyst was filtered (celite) and evaporated to give the amine as an off-white solid (12.97 g); NMR: 4.94 (s,2), 6.17 (s,1), 6.2 (d,1), 6.60 (t,2), 6.76 (d,1), 11.27 (bs,1); MS: 265(M+1).

b. 2,2-bis(Difluoromethyl)-6-iodo-3-oxo-3,4-dihydro-2H-1,4-benzoxazine. To a solution of the amine of step a. (12.94 g), 6N hydrochloric acid (30 mL) and water (30 mL) was added a solution of sodium nitrite (3.45 g) in water (30 mL) maintaining an internal temperature of abut 10° C. with vigorous stirring. The cold diazonium solution was slowly poured into a cold solution of potassium carbonate (10.4 g), diethylamine (5.5 g), and water (90 mL) with stirring. The aqueous solution was extracted with ethyl acetate. The combined organic extracts were washed (water, brine), and dried. Evaporation gave a red gum (16.36 g). This was dissolved in acetonitrile (150 mL and the solution was quickly added to a refluxing mixture of sodium iodide (7.64 g), BioRad AG50WX-12 resin (37.63 g, 5 mEq) and acetonitrile (180 mL) with vigorous stirring. After 5 hours of reflux, the resin was filtered, washed (methanol) and the filtrate evaporated. Chromatography, eluting with dichloromethane followed by 20% ether:hexanes, gave a solid that was stirred with dichloromethane:hexanes to give the iodide as a white powder (10.75 g); mp 181°–185 ° C.; NMR: 6.73 (t,2), 6.95 (d,1), 7.23 (s,1), 7.33 (d,1), 11.71 (s,1); MS: m/z=376(M+1).

c. 2,2-bis(Difluoromethyl)-6-phenylthio-3,4-dihydro-2H-1, 4-benzoxazin-3-one. A mixture of the iodide of step b. (3 g) tetrakistriphenylphosphine palladium (0.37 g), thiophenol (1.32 g) potassium tert-butoxide (3.50 g) and n-butanol (80 mL) was stirred and refluxed for 18 hours. The mixture was poured into excess 1N hydrochloric acid and extracted with ethyl acetate. The ethyl acetate was washed (water, brine), dried, and evaporated. Chromatography, eluting with 15% ethyl acetate:hexanes, gave the sulfide as white crystals (2.2 g); mp 129°–130 ° C.; NMR: 6.74 (t,2), 6.96 (s,1), 7.03 (d,1), 7.16 (d,1), 7.26–7.38 (m 5), 11.68 (s,1); MS: m/z=358(M+1).

d. 2,2-bis(Difluoromethyl)-6-phenylsulfonyl-3,4-dihydro-2H-1,4-benzoxazin-3-one. To a cold, stirred solution of potassium peroxymonosulfate (10.84 g) in water (40 mL) was added the sulfide of step c. (2.1 g) in methanol (50 mL). After 21 hours, the mixture was poured into water and the resulting solid was filtered, washed (water), and dried to give the sulfone as a white powder (2.03 g); mp 180°–183° C.; NMR: 6.77 (t,2), 7.35 (d,1), 7.51 (s,1), 7.60 to 7.75 (m,5), 7.92 (d,1), 11.92 (s,1); MS: m/z=390(M+1).

e. 2,2-bis(Difluoromethyl)-6-phenylsulfonyl-3,4-dihydro-2H-1,4-benzoxazine. The sulfone of step d. (2.02 g) was dissolved in dry tetrahydrofuran (50 mL) and cooled in an ice bath while borane (52 mL 1M solution in tetrahydrofuran) was slowly added. The clear solution was refluxed for 18 hours. Excess borane was destroyed with methanol and 6N hydrochloric acid (25 mL) while cooling and excess tetrahydrofuran was distilled. Water (25 mL) was added and reflux resumed for 2 hours. The mixture was extracted with ethyl acetate. The ethyl acetate extract was washed, (water, brine) and dried. Evaporation gave the 2,2-bis(difluoromethyl)-6-phenylsulfonyl-3,4-dihydro-2H-1,4-benzoxazine (1.9 g) as a white solid; mp 100°–113 ° C.; NMR: 3.44 (s,2), 6.41 (t,2), 6.65 (s,1), 7.07 (d,1), 7.17 (d,1), 7.29 (s,1), 7.59 to 7.71 (m,3), 7.88 (d,2); MS: m/z=376(M+1).

f. 2-(2,2-bis(Difluoromethyl)-6-phenylsulfonyl-3,4-dihydro-2H-1,4-benzoxazine-4-yl)pyridine. A mixture of the product of step e. (1 g), potassium carbonate (0.41 g), copper bronze (0125 g,), and 2-bromopyridine (4.3 g) was stirred and heated at 200° C. for 18 hours. The cooled, dark mixture was stirred with water and ethyl acetate:dichloromethane. The mixture was filtered through diatomaceous earth, and the lower organic layer was separated. The organic phase was washed (water), dried, and evaporated. Chromatography, eluting ethyl acetate:hexane (gradient 40% to 60%) gave the pyridine as a pale yellow gum (0.29 g); NMR: 4.31 (s,2), 6.49 (t,2), 7.06 (t,1), 7.21 (d,1), 7.33 (d,1), 7.53 (d,1), 7.60 to 7.70 (m,3), 7.79 (t,1), 7.92 (d,2), 7.94 (s,1), 8.36 (d,1); MS: m/z=453 (M+1).

EXAMPLE 7

2-(2-Ethyl-2-trifluoromethyl-6-nitro-3,4-dihydro-2H-1,4-benzoxazine-4-yl)pyridine-N-oxide. Sodium hydride (0.68 g, 60% in mineral oil) was added to a solution of 2-ethyl-2-trifluoromethyl-6-nitro-3,4-dihydro-2H-1,4-benzoxazine (0.235 g), 2-chloropyridine-N-oxide hydrochloride (0.142 g), and dimethylsulfoxide (10 mL) and stirred at room temperature overnight. The mixture was quenched with saturated ammonium chloride/water and extracted into ethyl acetate. The organic extract was washed (water, brine) dried, decolorized (charcoal), filtered (celite) and evaporated. Chromatography, eluting successively with dichloromethane, ethyl acetate, and then methanol, gave the title compound as a yellow solid (0.11 g); mp 59°–62 ° C.; NMR: 0.95 (t,3), 2.04 (q), 4.05 (d,d), 7.01 (s,1), 7.25 (d) 7.45 (m, 2), 7.63 (d), 7.76 (d), 8.41 (d,1); MS: m/z=370(M+1). Analysis for $C_{16}H_{14}F_3N_3O_4$: Calculated: C, 52.04; H, 3.82; N, 11.38; Found: C, 51.95; 3.98; N, 11.10.

a. N-(3-Nitro-6-fluorophenyl)-3,3,3-trifluoro-2-hydroxy-2-ethylpropanamide. A stirred solution of 2-hydroxy-2-trifluoromethylbutyric acid (1.2 g) and dimethylacetamide (10 mL) was cooled to −10° C. and treated dropwise with thionyl chloride (0.83 g). Stirring was continued at −10° C.

for 0.5 hours under nitrogen and 6-fluoro-3-nitroaniline was added. The mixture was stirred at room temperature overnight. The mixture was poured into water and extracted into ethyl acetate. The ethyl acetate layer was separated, washed (water), dried and evaporated. Chromatography, eluting with dichloromethane, gave the amide as an off-white solid (0.86 g); NMR: 0.92 (t,3), 1.84 (m,2), 2.11 (m,2), 7.54 (s,1), 7.62 (t,1), 8.18 (m,1), 8.56 (m,1), 10.03 (s,1); MS: m/z=311(M+1).

b. 2-Ethyl-2-trifluoromethyl-6-nitro-3-Oxo-3,4-dihydro-2H-1,4-benzoxazine. The amide from step a.(0.75 g), cesium fluoride (1.8 mg), and dimethylformamide (25 mL) was stirred at 100° C. for 18 hours. The cool reaction mixture was partitioned between brine and ethyl acetate. The combined ethyl acetate extracts were washed (brine), dried, and evaporated. The crude material was chromatographed, eluting with 15% ethyl acetate:hexanes, to give 2-Ethyl-2-trifluoromethyl-6-nitro-3-Oxo-3, 4-dihydro-2H-1,4-benzoxazine as an off-white solid (0.285 g); NMR: 0.986 (t,3), 2.04 (m,1), 2.35 (m,1), 7.33 (d,1), 7.81 (s,1) 7.92 (d,1), 11.87 (s,1); MS: m/z=291(M+1).

c. 2-Ethyl-2-trifluoromethyl-6-nitro-3,4-dihydro-2H-1,4-benzoxazine. The product of step b.(0.28 g) in tetrahydrofuran (10 mL) was cooled in an ice bath and treated with a 1M solution of borane tetrahydrofuran (4.8 mL). The clear solution was refluxed overnight. The solution was cooled (ice bath) and 6N HCl (10 mL) was added dropwise. The resulting solution was refluxed for 1.5 hour. The cooled solution was extracted with ethyl acetate. The combined extracts were washed (water, brine), dried, and evaporated to give the benzoxazine as a yellow solid (0.242 g); NMR: 0.97 (t,3), 1.88 (q,2), 3.44 (broad s,2), 6.8 (bs,1), 7.03 (d,1), 7.48 (d,1) 7.58 (s,1); MS: m/z=277(M+1).

EXAMPLE 8

2-(2,2-bis(Difluoromethyl)-6-nitro-3,4-dihydro-2H-1,4-benzoxazine-4-yl)pyridine-N-oxide.

2- (2,2-bis(difluoromethyl)-6-nitro-3,4-dihydro-2H-1,4-benzoxazine-4-yl)pyridine (1.32 g) 50% m-chloroperbenzoic acid (2.56 g), sodium bicarbonate (1.26 g), 1,2-dichloroethane (12 mL), water (12 mL), and butylhydroxymethylphenylsulfide (0.1 g) were stirred at reflux under nitrogen for 2 hours. Additional m-chloroperbenzoic acid (1.28 g), and Sodium bicarbonate (0.063 g) were added and reflux was continued overnight. The reaction mixture was cooled, diluted with dichloromethane and washed with sodium bicarbonate solution. The organic layer was separated, washed (water), dried and concentrated. Chromatography, eluting with dichloromethane followed by ethyl acetate, gave the title compound as a yellow amorphous solid (0.475 g); mp 138°–140 ° C.; NMR: 4.12 (s,2), 6.61 (t,2), 7.12 (s,1), 7.33 (d,1), 7.49 (m,2) 7.62 (d,1), 7.79 (d,1), 8.42 (d,1); MS: m/z=374(M+1). Analysis for $C_{15}H_{11}F_4N_3O_4$: Calculated: C, 48.27; H, 2.97; N, 11.26; Found: C, 48.30; H, 2.97; N, 11.25.

a. N-(3-Nitro-6-fluorophenyl)-3,3-difluoro-2-hydroxy-2-difluoromethylpropanamide. A stirred slurry of 3,3-difluoro-2-difluoromethyl-2-hydroxypropanoic acid (10 g), and dichloromethane (125 mL) was cooled to 0° C. and treated dropwise with thionyl chloride (6.8 g). Stirring was continued for 0.5 hour at 0° C. followed by addition of 6-fluoro-3-nitroaniline (8.2 g) and 4-dimethylaminopyridine (15.3 g). The mixture was stirred overnight. Additional thionyl chloride (6.8 g) was added and the resulting amber-colored solution was stirred overnight. The reaction mixture was then diluted with dichloromethane, washed (dilute hydrochloric acid, water), dried, and evaporated. Chromatography, eluting with dichloromethane (1 L) then 15% ethyl acetate:hexanes (0.9 L), gave the amide as a waxy, off-white solid (10 g); NMR: 6.47 (t,2), 7.63 (t,1), 8.1 (s,1), 8.19 (d,1) 8.47 (s,1) 10.15 (s,1); MS: m/z=315(M+1).

b. 2,2-bis(Difluoromethyl)-6-nitro-3,4-dihydro-2H-1,4-benzoxazin-3-one. A mixture of the amide from step a. (10 g), cesium fluoride (10 g) and dimethylformamide (75 mL) was stirred and heated at 130° C. for one hour. The cooled contents were poured into brine (800 mL) with vigorous stirring. The resulting solid was filtered, washed (water), and dried to give 2,2-bis(Difluoromethyl)-6-nitro-3,4-dihydro-2H-1,4-benzoxazin-3-one as a light orange solid (8.45 g); mp 178°–181° C.; NMR: 6.81 (t,2), 7.39 (d,1), 7.81 (s,1), 7.93 (d,1), 12.6 (s,1); MS: m/z=295(M+1).

c. 2,2-bis(difluoromethyl)-6-nitro-3,4-dihydro-2H-1,4-benzoxazine. The product of step b. (2 g) was dissolved in tetrahydrofuran (80 mL) and borane (68 mL, 1M in tetrahydrofuran) was added dropwise. The clear solution was refluxed overnight. Excess borane was destroyed with methanol followed by 6N hydrochloric acid (40 mL). The mixture was concentrated, diluted with water (40 mL), and extracted with ethyl acetate. The ethyl acetate was washed (water, brine), dried, and evaporated to give the 2,2-bis (difluoromethyl)-6-nitro-3,4-dihydro-2H-1,4-benzoxazine as a yellow solid (1.78 g); mp 150°–152° C.; NMR: 3.51 (s,2), 6.46 (t,2), 6.81 (s,1), 7.09 (d,1), 7.51 (d,1), 7.62 (s,1); MS: m/z=281(M+1).

d. 2-(2,2-bis(Difluoromethyl)-6-nitro-3,4-dihydro-2H-1,4-benzoxazine-4-yl)pyridine. The product of step c. (0.81 g) potassium carbonate (1.6 g), copper bronze (0.37 g), 2-bromopyridine (0.83 mL), 18-crown-6 (0.079 g), and 1,2-dichlorobenzene (8 mL) were stirred and heated at 170° C. for six hours. The reaction mixture was cooled, diluted with dichloromethane and chromatographed, eluting with dichloromethane, to give the pyridine as a light amber syrup (0.77 g); NMR: 4.34 (s,2), 6.55 (t,2), 7.07 (m,1), 7.37 (m,2), 7.82 (m,2), 8.23 (s,1), 8.39 (d,1); MS: m/z=358(M+1).

EXAMPLE 9

2-(S)-(−)-(2-Methyl-2-trifluoromethyl-6-nitro-3,4-dihydro-2H-1,4-benzoxazine-4-yl)pyridine N-oxide hydrochloride.

A solution of 2-(S)-2-methyl-2-trifluoromethyl-6-nitro-3, 4-dihydro-2H-1,4-benzoxazine (500 mg) and 2-chloropyridine-N-oxide hydrochloride (320 mg) in dimethylsulfoxide (18 mL) was treated with sodium hydride (60% dispersion in oil, 153 mg) while at 15° C. The reaction was stirred for an additional 18 hours at room temperature. The mixture was then poured onto ice water and extracted with ethyl acetate. The combined organic portions were evaporated under reduced pressure to a brown liquid. Chromatography of this liquid on silica gel eluting with ethyl acetate:hexane (20:80 then 1:1) provided a yellow oil (200 mg). A solution of this oil in diethyl ether (30 mL) was treated with HCl/ether (4 mL). The hydrochloride salt oiled out of solution. Trituation with a solution of dichloromethane in an excess of diethylether provided the title compound as a yellow solid (150 mg); mp 171°–174 ° C.; (250 MHZ) NMR: 1.60 (s,3), 4.03 (m,2), 7.04 (s,1), 7.23 (dd,1), 7.42 (m,2), 7.65 (d,1), 7.76 (m,1), 8.41 (d,1); MS: m/z=356(M+1); $[\alpha]_D=-29$ (methanol). Analysis for $C_{15}H_{12}F_3N_3O_4 \cdot HCl$: Calculated: C, 45.99; H, 3.35; N, 10.73; Found: C, 45.91; H, 3.44; N, 10.51.

a. Methyl (S)-2-hydroxy-2-methyl-3,3,3-trifluoropropanoate. A solution of (S)-2-hydroxy-2-methyl-3,3,3-trifluoropropanoic acid (14.94 g) and concentrated sulfuric acid (2.85 mL) in methanol (25 mL) was stirred at reflux for 18 hours. The excess methanol was distilled from the solution and the cooled mixture was poured into ice water (75 mL) and extracted with dichloromethane. The combined organic portions were dried and evaporated to give the ester as a yellow oil; 250 MHz NMR: 1.49 (s,3), 3.75 (s,3), 7.00 (s,1); MS: m/z=173(M+1).

b. 2-(S)-2-Methyl-2-trifluoromethyl-6-nitro-3-oxo-3,4-dihydro-2H-1,4-benzoxazine. A mixture of methyl (S)-2-hydroxy-2-methyl-3,3,3-trifluoropropanoate (7.00 g) 6-fluoro-3-nitroaniline (6.35 g), and cesium fluoride (18.55 g) in dimethylformamide (185 mL) was stirred at 120° C. for 6.5 hours. The dimethylformamide was removed by evaporation (65° C.). The residue was partitioned between ethyl acetate (200 mL) and water (200 mL). The organic layer was washed (saline), dried ($MgSO_4$), and evaporated to give a brown oil. Chromatography, eluting with dichloromethane (2 L), chloroform (3 L), and methanol:chloroform (5:95) provided 2-(S)-2-Methyl-2-trifluoromethyl-6-nitro-3-oxo-3,4-dihydro-2H-1,4-benzoxazine aa a brown oil (5.44 g); NMR: 1.79 (s,3), 7.31 (d,1), 7.81 (d,1), 7.93 (m,1), 11.76 (s,1); MS: m/z=277(M+1).

c. 2-(S)-2-Methyl-2-trifluoromethyl-6-nitro-3,4-dihydro-2H-1,4-benzoxazine. A solution of the product of step b. (5.44 g) in tetrahydrofuran (65 mL) was treated with diborane (104 mL, 1M in tetrahydrofuran). The solution was alowed to reflux for 48 hours, was cooled, and 6N HCl (20 mL) was added. The solution was allowed to reflux 2.5 hours, the solvent was evaporated, and the remaining brown liquid was partitioned between dichloromethane and water. The organic layer was washed with pH=7 buffer (3×300 mL), dried ($MgSO_4$), and evaporated to give a brown oil. Chromatography, eluting with diethyl ether:hexane (30:70), provided the benzoxazine as a yellow solid (2.39 g); mp 133.5°–135.6° C.; 250 MHZ NMR: 1.48 (s,3), 3.41 (m,2), 6.82 (s,1), 7.01 (d,1), 7.48 (dd,1), 7.59 (d,1); MS: m/z=263 (M+1); $[\alpha]_D=+3.82$ (in methanol). Analysis for $C_{10}H_9F_3N_2O_3$: Calculated: C, 45.81; 3.46; N, 10.68; Found: C, 46.06; 3.65; N, 10.68.

EXAMPLE 10

2-(S)-(+)-(2-Methyl-2-trifluoromethyl-6-nitro-3,4-dihydro-2H-1,4-benzoxazine-4-yl)-5-trifluoromethylpyridine N-oxide.

A mixture of 2-(S)-(2-methyl-2-trifluoromethyl-6-nitro-3,4-dihydro-2H-1,4-benzoxazine-4-yl)-5-trifluoromethylpyridine (250 mg), metachloroperbenzoic acid (190 mg), 3-tert-butyl-4-hydroxy-5-methylphenylsulfide in dichloromethane (15 mL) was heated at reflux for 24 hours. Thin layer chromatography of a reaction aliquot showed the reaction to be incomplete. To the cooled reaction an additional amount of metachloroperbenzoic acid (190 mg) and 3-tert-butyl-4-hydroxy-5-methylphenylsulfide was added and the reaction mixtures heated to reflux 24 hours. The cooled reaction mixture was poured onto water, extracted with ethyl acetate (2×50 mL). The combined organic layer washed with 10% sodium bisulfite (4×50 mL), washed (water) (1×50 mL), dried ($Na_2SO_4$), and evaporated to an oil. Chromatography, eluting with ethyl acetate:hexane (20:80) provided an oil-solid mixture (140 mg). This mixture was partitioned between water (20 mL) and diethyl ether (50 mL). The organic layer was dried ($MgSO_4$), and evaporated to a yellow solid (60 mg) which was recrystallised from ethanol/hexane to provide the title compound (20 mg); mp 172.5–174.5° C.; $[\alpha]_D$(methanol)+41; NMR (300 MHz, $d_6$-DMSO): 1.56 (s,3), 4.11 (s,2H, CH2), 7.26 (d), 7.35 (s,1), 7.82(m,3), 8.91 (s,1); Ms (CI): m/z=424(M+1). Analysis for $C_{16}H_{11}F_6N_3O_4$: Calculated: C, 45.40; H, 2.62; N, 9.92; Found: C, 45.17; H, 2.73; N, 9.77.

The necessary starting material was prepared following a method similar to that described in Example 9, but using 5-trifluoromethyl-2-chloropyridine instead of 2-chloropyridine-N-oxide hydrochloride.

EXAMPLE 11

The following illustrate representative pharmaceutical dosage forms containing a compound of formula I, for example as illustrated in any of the previous Examples, (hereafter referred to as "compound X"), for therapeutic or prophylactic use in humans:

|  | mg/tablet |
|---|---|
| (a) Tablet | |
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |
| (b) Capsule | |
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

CHEMICAL FORMULAE

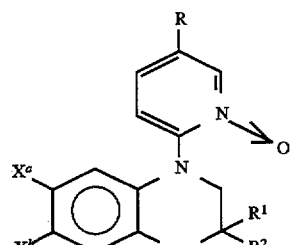

I

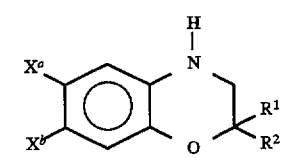

II

-continued
CHEMICAL FORMULAE

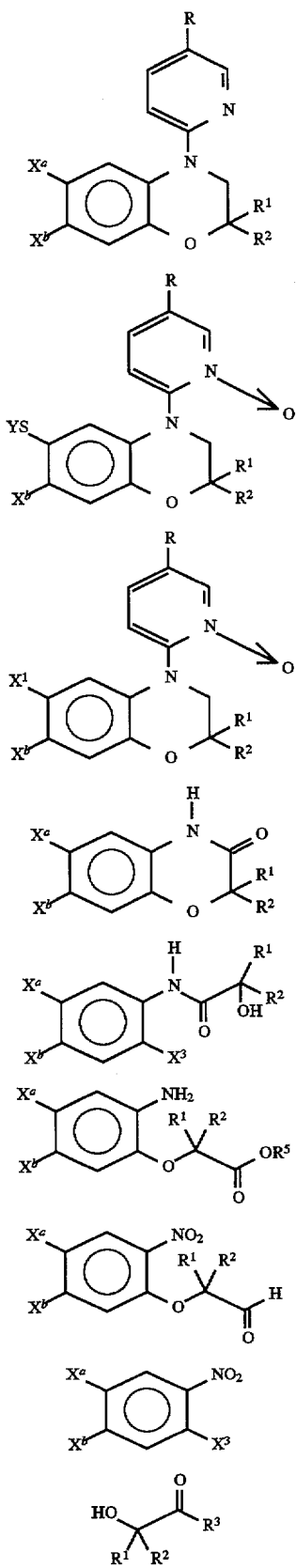

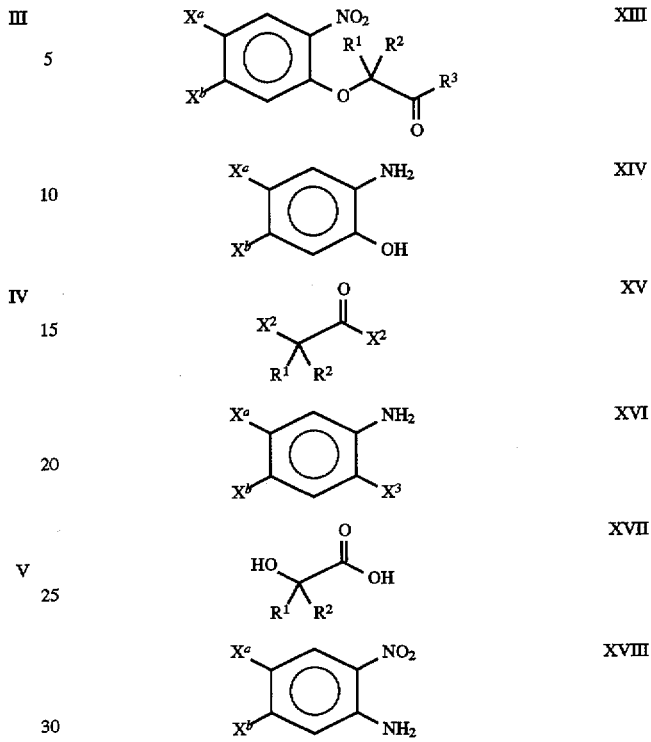

What is claimed is:
1. A method of treating asthma comprising administering to a mammal in need of such treatment an effective amount of a compound of formula I:

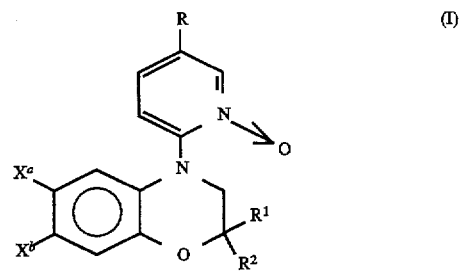

(I)

wherein,

R is hydrogen or trifluoromethyl $R^1$ and $R^2$ are independently selected from (1–3C)alkyl which may be substituted by one or more fluoro groups, provided that at least one of $R^1$ and $R^2$ is substituted by at least one fluoro group;

$X^a$ is selected from
(A) cyano, nitro, trifluoromethyl, pentafluoroethyl, trifluoromethoxy, trifluoromethylsulfonyl, methylsulfonyl, halo or trifluoromethylthio, and
(B) a group Y–Z connected to the benzo ring through Z, wherein Y is a 6-membered aromatic ring or a 6-membered heteroaromatic ring containing 1–2 nitrogens as the heteroatoms and is connected to Z through carbon, and Z is selected from sulfonyl and carbonyl; and $X^b$ is selected from hydrogen, halogen, trifluoromethyl, trifluoromethylacetamido and (1–4C)alkoxy; or $X^a$ and $X^b$, together with the carbon atoms to which they are attached, form an 1-oxa-2,5-diazole, a 1-thia-2,5- diazole or a 1,2,5-triazole ring; or a pharmaceutically acceptable salt of said compound.

2. The method of claim 1 wherein in the compound of Formula I

R is hydrogen or trifluoromethyl $R^1$ and $R^2$ are independently selected from (1–3C)alkyl which may be substituted by one or more fluoro groups, provided that at least one of $R^1$ and $R^2$ is substituted by at least one fluoro group;

$X^a$ is selected from (A) cyano, nitro, trifluoromethyl, pentafluoroethyl, trifluoromethoxy, trifluoromethylsulfonyl, methylsulfonyl, trifluoromethylthio, and (B) a group Y–Z connected to the benzo ring through Z, wherein Y is a 6-membered aromatic ring or a 6-membered heteroaromatic ring containing 1–2 nitrogens as the heteroatoms and is connected to Z through carbon, and Z is selected from sulfonyl and carbonyl; and $X^b$ is selected from hydrogen, halogen, trifluoromethyl, trifluoromethylacetamido and (1–4C)alkoxy; or $X^a$ and $X^b$, together with the carbon atoms to which they are attached, form an 1-oxa-2,5-diazole, a 1-thia-2,5-diazole or a 1,2,5-triazole ring; or a pharmaceutically acceptable salt of said compound.

3. A method of claim 1, wherein in the compound of formula I, $R^1$ and $R^2$ are independently selected from methyl, monofluoromethyl, difluoromethyl, trifluoromethyl, ethyl, and pentafluoroethyl.

4. A method of claim 1, wherein in the compound of formula I $X^a$ is 4-pyridylsulfonyl, 3-pyridylsulfonyl, phenylcarbonyl, 2-pyridylsulfonyl, 2-pyridylcarbonyl, cyano, nitro, trifluoromethyl, trifluoromethoxy, pentafluoroethyl, phenylsulfonyl, methylsulfonyl, trifluoromethylthio or trifluoromethylsulfonyl;

$X^b$ is hydrogen, chlorine, trifluoromethyl, trifluoromethyl-acetamido or methoxy; or $X^a$ and $X^b$ taken together with the carbon atom to which they are attached is 1-oxa-2,5-diazole.

5. The method of claim 1, wherein in the compound of formula I $X^a$ is 4-pyridylsulfonyl, 3-pyridylsulfonyl, 2-pyridylsulfonyl, 2-pyridylcarbonyl, cyano, nitro, trifluoromethyl, trifluoromethoxy, pentafluoroethyl, phenylsulfonyl, methylsulfonyl, trifluoromethylthio or trifluoromethylsulfonyl;

$X^b$ is hydrogen, chlorine, trifluoromethyl, trifluoromethyl-acetamido or methoxy; or $X^a$ and $X^b$ taken together with the carbon atom to which they are attached is 1-oxa-2,5-diazole.

6. The method of claim 1, wherein in the compound of formula I, $R^1$ is methyl or ethyl, and $R^2$ is trifluoromethyl; or in which $R^1$ and $R^2$ are each difluoromethyl.

7. The method of claim 2, wherein in the compound of formula I, $R^1$ is methyl or ethyl, and $R^2$ is trifluoromethyl or in which $R^1$ and $R^2$ are each difluoromethyl.

8. The method of claim 3, wherein in the compound of formula I, $R^1$ is methyl or ethyl and $R^2$ is trifluoromethyl; or wherein $R^1$ and $R^2$ are each difluoromethyl.

9. The method of claim 4, wherein in the compound of formula I, $R^1$ is methyl or ethyl and $R^2$ is trifluoromethyl; or wherein $R^1$ and $R^2$ are each difluoromethyl.

10. The method of claim 5, wherein in the compound of formula I, $R^1$ is methyl or ethyl and $R^2$ is trifluoromethyl; or wherein $R^1$ and $R^2$ are each difluoromethyl.

11. The method of claim 1, wherein the compound is selected from: 2-(2-methyl-2-trifluoromethyl-6-phenylsulfonyl-3,4-dihydro-2H-1,4-benzoxazin-4-yl)pyridine-N-oxide; S-(+)-2-(2-methyl-2-trifluoromethyl6-phenylsulfonyl-3,4-dihydro-2H-1,4-benzoxazine-4-yl)pyridine-N-oxide; R-(−)-2-(2-methyl-2-trifluoromethyl-6-phenylsulfonyl-3,4-dihydro-2H-1,4-benzoxazine-4-yl)pyridine-N-oxide; 2-(2,2-(bis)fluoromethyl-6-nitro-3,4-dihydro-2H-1,4-benzoxazine-4-yl)pyridine-N-oxide; 2-(2,2-(bis)fluoromethyl-6-phenylsulfonyl-3,4-dihydro-2H-1,4-benzoxazine-4-yl)pyridine-N-oxide; 2-(2,2-bis(difluoromethyl)-6-phenylsulfonyl-3,4-dihydro-2H-1,4-benzoxazine-4-yl)pyridine-N-oxide; 2-(2-ethyl-2-trifluoromethyl-6-nitro-3,4-dihydro-2H-1,4-benzoxazine-4-yl)pyridine-N-oxide; 2-(2,2-bis(difluoromethyl)-6-nitro-3,4-dihydro-2H-1,4-benzoxazine-4-yl)-pyridine-N-oxide; 2-(S)-(+)-(2-methyl-2-trifluoromethyl-6-nitro-3,4-dihydro-2H-1,4-benzoxazine-4-yl)pyridine-N-oxide; and 2-(S)-(+)-2-(2-methyl-2-trifluoromethyl-6-nitro-3,4-dihydro-2H-1,4-benzoxazine-4-yl)-5-trifluoromethylpyridine-N-oxide; and pharmaceutically acceptable salts thereof.

12. The method of claim 1, wherein the compound is selected from 2-(2,2-bis-(difluoromethyl)-6-nitro-3,4-dihydro-2H-1,4-benzoxazine-4-yl)-pyridine-N-oxide; and pharmaceutically acceptable salts thereof.

* * * * *